US006936569B2

(12) United States Patent
Penner et al.

(10) Patent No.: US 6,936,569 B2
(45) Date of Patent: Aug. 30, 2005

(54) COMPOSITIONS AND METHODS FOR PROTECTING CULTIVATED PLANTS FROM HERBICIDAL INJURY

(75) Inventors: Donald Penner, Williamston, MI (US); Christy L. Sprague, Urbana, IL (US); Richard F. Burow, Midland, MI (US)

(73) Assignees: Board of Trustees of Michigan State University, East Lansing, MI (US); Dow Corning Corporation, Midland, MI (US)

( * ) Notice: Subject to any disclaimer, the term of this patent is extended or adjusted under 35 U.S.C. 154(b) by 420 days.

(21) Appl. No.: 09/777,320

(22) Filed: Feb. 6, 2001

(65) Prior Publication Data

US 2002/0010096 A1 Jan. 24, 2002

Related U.S. Application Data

(63) Continuation of application No. 09/353,410, filed on Jul. 15, 1999, now Pat. No. 6,235,682.

(60) Provisional application No. 60/092,993, filed on Jul. 16, 1998.

(51) Int. Cl.[7] .................................................. A01N 3/02

(52) U.S. Cl. .................................................. 504/116.1

(58) Field of Search ............................... 504/116.1, 118

(56) References Cited

U.S. PATENT DOCUMENTS

| | | | | |
|---|---|---|---|---|
| 3,294,725 A | | 12/1966 | Findlay et al. | |
| 4,626,274 A | * | 12/1986 | Hausmann et al. | 71/93 |
| 5,051,129 A | | 9/1991 | Cuthbert et al. | |
| 5,073,195 A | | 12/1991 | Cuthbert et al. | |
| 5,627,131 A | | 5/1997 | Shribbs et al. | |
| 5,631,210 A | * | 5/1997 | Tseng | 504/282 |
| 5,780,412 A | | 7/1998 | Scarborough et al. | |

FOREIGN PATENT DOCUMENTS

| | | | |
|---|---|---|---|
| DE | 19635060 | * | 3/1998 |
| JP | 9631121 | * | 10/1996 |

OTHER PUBLICATIONS

Bhowmik and Prostak, Weed Sci. Soc. Am. Abstr. 36: 13 (1996).

Boldt and Putnam, Weed Science 28:474–477 (1980).

Curvey and Kapusta, North Central Weed Sci. Soc. 51:57–58 (1996).

DeRuiter et al, Weed Sci. 38:567–572 (1990).

Geier and Stahlman, North Central Weed Sci. Soc. 52:81 (1997).

Luscombe et al, Proc. North Central Weed Sci. Soc. 59:57–58 (1994).

Luscombe and Pallet, Pestic. Outlook 29–32 (1996).

Mosier et al., Proc. North Central Weed Sci. Soc. 50:74 (1995).

Obermeier, et al., Proc. North Central Weed Sci. Soc. 50:25 (1995).

(Continued)

*Primary Examiner*—Alton Pryor
(74) *Attorney, Agent, or Firm*—Ian C. McLeod

(57) ABSTRACT

Compositions comprising a herbicide wherein it is desired that the compound not be retained by the plant foliage, and a repellant adjuvant, wherein the repellant modifies the surface properties of the composition so that retention of the composition on foliage of a cultivated plant is reduced are described. In particular, the herbicide composition comprises a repellant adjuvant that is an aqueous solution of an alkyltrialkoxysilane such as methyltrimethoxysilane and a water soluble silane coupling agent such as N-(2-aminoethyl)-3-aminopropyltrimethoxysilane or an aqueous solution of an organosiliconate such as sodium methyl siliconate. Methods are described for using these compositions to prevent weeds without injury to cultivated plants, which plants include crop plants, food plants, turfgrass, ornamental plants, and garden plants.

17 Claims, 2 Drawing Sheets

OTHER PUBLICATIONS

Pallett et al., Pestic. Sci. 50:83–84 (1997).
Pallett et al., Pestic. Biochem. Physiol. 62:113–124 (1998).
Simkins et al., Proc. North Central Weed Sci. Soc. 50:25 (1995).
Sprague et al., Weed Sci. Soc. Amer. Abstr. 37: 5 (1997).
Stevens et al., Pestic. Sci. 38:237–245 (1993).
Veilleux et al., North Central Weed Sci. Soc. 50:75 (1995).
Viviani et al., Pestic. Biochem. Physiol. 62:125–134 (1998).
Vrabel et al., Proc. North Central Weed Sci. Soc. 50:24–25 (1995).
Wrucke et al., Proc. North Central Weed Sci. Soc. 52:17 (1997).
Young et al., Weed Sci. Soc. Am. Abstr. 38: 8 (1998).
Young and Hart, Weed Sci. 46:397–402 (1998).

* cited by examiner

COMPOSITIONS AND METHODS FOR PROTECTING CULTIVATED PLANTS FROM HERBICIDAL INJURY

CROSS-REFERENCE TO RELATED APPLICATION

This application claims priority to U.S. Provisional Application Ser. No. 60/092,993 which was filed on Jul. 16, 1998 and a continuation No. 09/353,410 filed Jul. 15, 1999 now U.S. Pat. No. 6,235,692.

STATEMENT REGARDING FEDERALLY SPONSORED RESEARCH OR DEVELOPMENT

None.

BACKGROUND OF THE INVENTION (1) Field of the Invention

The present invention relates to compositions comprising a herbicide, or combinations of herbicides, with or without a safener, and a repellent adjuvant, wherein the repellent adjuvant modifies the surface properties of the composition so that retention of the composition on foliage of the cultivated plant is reduced. In particular, the herbicide composition comprises a repellent adjuvant that is an aqueous solution of an an alkyltrialkoxysilane such as methyltrimethoxysilane and a water soluble silane coupling agent such as N-(2-aminoethyl)-3-aminopropyltrimethoxysilane or an aqueous solution of an organosiliconate such as sodium methyl siliconate.

(2) Description of Related Art

Many herbicides will cause injury to certain crop plants when applied in amounts that are effective in controlling weed growth. The damage to crop plants can be particularly severe when the crop plant is in an early stage of development, which is precisely the time when control of weed growth is most important. For this reason many herbicides are unsuitable for controlling weeds when crop plants are at particular stages of growth. Therefore, the inability to control weed growth results in lower crop yield and reduced crop quality because the weeds compete with the crop plant for nutrients, light and water. In an attempt to broaden the usefulness of various herbicides, various herbicide compositions have been developed which contain compounds known as “safeners”, also referred to as “antidotes”, “protectants” or “antagonists.”

The concept of using safeners to enhance the tolerance of crops to herbicides was developed in the late 1940’s and has led to the development of particular herbicidal compositions that have the ability to control weed growth but without adversely affecting the growth or yield of a particular crop plant. However, the identification of an antidote which safens a particular class of herbicide or mixture of herbicides is not a theoretical determination but must be determined empirically. This determination is performed by observing the complex interaction of many biological and chemical factors, including the type of herbicide, the weed species to be controlled, the crop plant to be protected from weed competition and herbicidal injury, the developmental stage of the crop plant, and the safening compound itself. Moreover, the safener and herbicide must possess physicochemical properties which allow an environmentally acceptable and stable product to be prepared. Therefore, because the discovery of herbicide/safener compositions is so empirically based, the development of effective herbicide/safener combinations is an expensive and unpredictable undertaking.

Isoxaflutole, an isoxazole herbicide, is a new soil-applied herbicide for use in corn. Researchers have reported that isoxaflutole provides excellent preemergence control of several broadleaf and annual grass weed species at rates ranging from 53 g/ha to 158 g/ha in conventional tillage and no-tillage corn (Bhowmik and Prostak, Weed Sci. Soc. Am. Abstr. 36: 13 (1996); Curvey and Kapusta, North Central Weed Sci. Soc. 51: 57–58 (1996); Geier and Stahlman, North Central Weed Sci. Soc. 52: 81 (1997); Luscombe et al., Proc. North Central Weed Sci. Soc. 59: 57–58(1994); Mosier et al., Proc. North Central Weed Sci. Soc. 50: 74 (1995); Obermeier et al., Proc. North Central Weed Sci. Soc. 50: 25 (1995); Simkins et al., Proc. North central Weed Sci. Soc. 50: 25 (1995); Veilleux et al., North central Weed Sci. Soc. 50: 75 (1995); Vrabel et al., Proc. North Central Weed Sci. Soc. 24–25 (1995); Wrucke et al., Proc. North Central Weed Sci. Soc. 52: 17(1997); and Young et al., Weed Sci. Soc. Am. Abstr. 38: 8 (1998)). The mode of action of isoxaflutole is the competitive inhibition of the 4-hydroxyphenylpyruvate dioxygenase enzyme (EC 1.13.11.27) (Pallett et al., Pestic. Biochem. Physiol. 62: 113–124 (1998); Viviani et al., Pestic. Biochem. Physiol. 62: 125–134 (1998)). Inhibition of this enzyme disrupts carotenoid biosynthesis causing a bleaching symptomology in susceptible species similar to herbicides that disrupt carotenoid biosynthesis by targeting the phytoene desaturase enzyme (Luscombe and Pallet, Pestic. Outlook, 29–32 (1996); and Pallett et al., Pestic. Sci. 50: 83–84 (1997)). While isoxaflutole has been shown to be an effective herbicide for controlling weeds, isoxaflutole also has been shown to cause injury to corn and other crop plants, especially when applied postemergent. For an example, see U.S. Pat. No. 5,627,131 to Shribbs et al.

Therefore, there is a need for a method for applying a herbicide post-emergence to a wide variety of cultivated plants that does not depend on the identity of the herbicide or the use of a safener. Such a composition would not be injurious to the cultivated plant but would maintain its ability to control weeds. The present invention provides compositions and methods for their use that satisfy this need.

SUMMARY OF THE INVENTION

The present invention provides compositions comprising a herbicide, or a combination of herbicides, with or without a safener, and a repellent adjuvant which modifies the surface properties of the composition so that retention of the composition on foliage of the cultivated plant is reduced. An important element of the composition is the repellent adjuvant. When the repellent adjuvant is mixed with the herbicide or combination of herbicides, with or without a safener, to form the composition of the present invention and applied to the plants with a sprayer, the emitted composition spray forms spherical particles which then bounce off the plant foliage. In this manner the repellent adjuvant prevents retention of the composition by the plant. Thus, herbicidal injury to the cultivated plant is reduced because the herbicide composition is directed to the soil. Therefore, the present invention is particularly useful when it comprises herbicides that exert their primary effects at the soil.

The present invention provides a composition for protecting cultivated plants comprising (a) at least one herbicide and (b) a repellent adjuvant for modifying the surface properties of the composition so that retention of the composition on foliage of the cultivated plant is reduced. The composition of the present invention further comprises compositions wherein the herbicide is selected from the group consisting of acetanilides, acetamides, acetolactate synthase inhibitors, isoxazoles, diketonitriles, triketonitriles dinitroanilines, triazines, substituted ureas, ethofumerates, isoxafen, oxodiazon, dithiopyr and combinations thereof. Further still, the composition of the present invention comprises a composition wherein the composition further comprises a safener. In particular embodiments of the present invention, the safener is selected from the group consisting of MON 4660, 2,2-dichloro-N,N-di-2-propenylacetamide, 3-dichloroacetyl-5-(2-furanyl)-2,2-dimethyl-oxazolidine, 2,2,5-trimethyl-N-dichloroacetyloxazolidine, 2,2-dimethyl-5-phenyl-N-dichloroacetyl oxazolidine, N,N-diallyl-2,2-dichloroacetamide, 2,2-dimethyl-5(2-furanyl)-N-dichloroacetyl oxazolidine, 2,2-dimethyl-5(2-thienyl)-N-dichloroacetyl oxazolidine, 2,2-spirocyclohexy-N-dichloroacetyl oxazolidine, 4-(dichloroacetyl)-3,4-dihydro-3-methyl-2H-1,4-benoxazine, 3-[3-(dichloroacetyl)-2,2-dimethyl-5-oxalidinyl]pyridine, 4-(dichloroacetyl)-1-oxa-4-azapiro-(4,5)-decane, 2,2-dichloro-1-(1,2,3,4-tetrahydro-1-methyl-2-isoquinolyl)ethanone, cis/trans-1,4-bis (dichloroacetyl)-2,5-dimethylpiperazine, N-(dichloroacetyl)-1,2,3,4-tetrahydroquinaldine, 1,5-bis (dichloroacetyl)-1,5-diazacyclononane, 1-(dichloroacetyl)-1-azaspiro[4,4]nonane, and combinations thereof.

The present invention further provides a method for reducing injury to cultivated plants, by the herbicide, by applying as a spray at least one herbicide with or without a safener in a composition with the repellent adjuvant which modifies the surface properties of the composition so that retention of the composition on foliage of the cultivated plant is reduced. The present invention provides a method for protecting cultivated plants, the composition comprising (a) a t least one herbicide and (b) a repellent adjuvant for modifying the surface properties of the composition so that retention of the composition on foliage of the cultivated plant is reduced. The present invention further provides a method for using a composition wherein the herbicide is selected from the group consisting of acetanilides, acetamides, acetolactate synthase inhibitors, isoxazoles, diketonitriles, triketonitriles dinitroanilines, triazines, substituted ureas, ethofumerates, isoxafen, oxodiazon, dithiopyr and combinations thereof. Further still, the present invention provides a method for using the composition wherein the composition further comprises a safener. In particular embodiments of the present invention, the safener is selected from the group consisting of 2,2-dichloro-N,N-di-2-propenylacetamide, 3-dichloroacetyl-5-(2-furanyl)-2,2-dimethyl-oxazolidine, 2,2,5-trimethyl-N-dichloroacetyloxazolidine, 2,2-dimethyl-5-phenyl-N-dichloroacetyl oxazolidine, N,N-diallyl-2,2-dichloroacetamide, 2,2-dimethyl-5(2-furanyl)-N-dichloroacetyl oxazolidine, 2,2-dimethyl-5(2-thienyl)-N-dichloroacetyl oxazolidine, 2,2-spirocyclohexy-N-dichloroacetyl oxazolidine, 4-(dichloroacetyl)-3,4-dihydro-3-methyl-2H-1,4-benoxazine, 3-[3-(dichloroacetyl)-2,2-dimethyl-5-oxalidinyl]pyridine, 4-(dichloroacetyl)-1-oxa-4-azapiro-(4,5)-decane, 2,2-dichloro-1-(1,2,3,4-tetrahydro-1-methyl-2-isoquinolyl)ethanone, cis/trans-1,4-bis (dichloroacetyl)-2,5-dimethylpiperazine, N-(dichloroacetyl)-1,2,3,4-tetrahydroquinaldine, 1,5-bis (dichloroacetyl)-1,5-diazacyclononane, 1-(dichloroacetyl)-1-azaspiro[4,4]nonane, and combinations thereof.

To make the composition of the present invention or to practice the method of the present invention, it is preferable that the repellent adjuvant be selected from the group consisting of an aqueous solution of an alkali metal organosiliconate and an aqueous solution of a water soluble siloxane solution. The organosiliconate having the formula:

$$(RsiO_{3/2})_a(X_2O)_b$$

wherein X denotes sodium or potassium, and R is methyl, ethyl, or propyl, and the ration of Si:X is about 1:1; and an aqueous solution of a water soluble coupling agent and an alkyltrialkoxysilane selected from the group consisting of alkyltrialkoxysilanes with C1 to C6 alky groups on silicon and a blend of alkyltrialkoxysilanes each with a C1 to C6 alkyl groups on silicon. In a preferred embodiment, the repellent adjuvant is selected from the group consisting of an aqueous solution of sodium methyl siliconate and an aqueous solution of N-(2-aminoethyl)-3-aminopropyltrimethoxysilane and methyltrimethoxysilane.

OBJECTS

Therefore it is an object of the present invention to provide herbicide compositions that can be applied postemergence which do not injure cultivated plants while maintaining the herbicide's ability to effectively control weeds.

These and other objects will become increasingly apparent through the following detailed description of the invention and examples.

DESCRIPTION OF PREFERRED EMBODIMENTS

Figure 1:
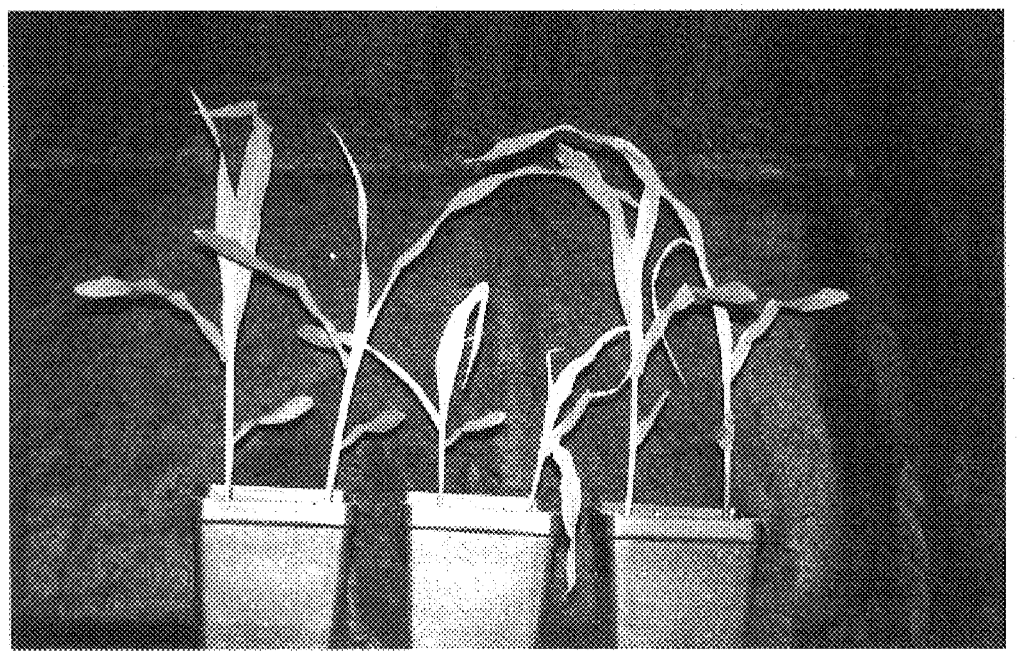
FIG. 1 is a photograph that shows the ability of the composition of the present invention comprising an aqueous solution of sodium methyl siliconate to prevent corn injury. The corn plants were treated from left to right: untreated control, corn treated with isoxaflutole in combination with DUAL II (metolachlor and benoxacor), and corn treated with a composition of the present invention (a combination of isoxaflutole, DUAL II, and sodium methyl siliconate). The sodium methyl siliconate was applied at a rate 0.25%. The photograph shows the corn 8 days after treatment.
Figure 2:
FIG. 2 is a photograph that shows the ability of the composition of the present invention comprising an aqueous solution of N-(2-aminoethyl)-3-aminopropyltrimethoxysilane and methyltrimethoxysilane to prevent corn injury. The corn plants were treated from left to right: untreated control, corn treated with a combination of isoxaflutole and DUAL II, and corn treated with a composition of the present invention (a combination of isoxaflutole, DUAL II, and an aqueous solution of N-(2-aminoethyl)-3-aminopropyltrimethoxysilane and methyltrimethoxysilane). The aqueous solution of N-(2-aminoethyl)-3-aminopropyltrimethoxysilane and methyltrimethoxysilane was applied at a rate 0.25%. The photograph shows the corn 8 days after treatment.

The present invention provides a composition for protecting cultivated plants comprising a herbicide, or combination of herbicides, with or without a safener, and a repellent adjuvant for modifying the surface properties of the composition so that retention of the composition on foliage of the cultivated plant is reduced. The herbicide comprising the present invention can be selected from the group consisting of acetanilides, acetamides, acetolactate synthase inhibitors, isoxazoles, diketonitriles, triketonitriles, dinitroanilines, triazines, substituted ureas, ethofumerates, isoxafen, oxadiazon, dithiopyr and combinations thereof. In particular, it is desirable that the herbicide or combination of herbicides exert their primary effects at the soil. The repellent adjuvant comprising the composition is a silicone-based aqueous solution that forms an emulsion when in combination with the herbicide, which has modifies properties. The emulsion forms spherical particles when sprayed from a sprayer. The spherical particles bounce off the foliage of the plant to the ground where the herbicide then exerts its effect. One type of repellent adjuvant suitable for use in the present invention is exemplified by an aqueous solution of the organosiliconate having the formula:

$$(RSiO_{3/2})_a(X_2O)_b$$

wherein X denotes sodium or potassium, and R is methyl, ethyl, or propyl, and the ratio of Si:X is about 1:1. In a preferred embodiment of an adjuvant of this type, the organosiliconate is sodium methyl siliconate, potassium methyl siliconate, or a mixture thereof. In a most preferred embodiment, the aqueous solution of organosiliconate consists essentially of 32 weight percent of sodium methyl siliconate and 67 weight percent of water. A second type of repellent adjuvant suitable for use in the present invention is an aqueous solution of a water soluble silane coupling agent and an alkyltrialkoxysilane, the alkyltrialkoxysilane being selected from the group consisting of alkyltrialkoxysilanes with C1 to C6 alkyl groups on silicon and a blend of alkyltrialkoxysilanes each with a C1 to C6 alkyl groups on silicon, the alkyltrialkoxysilane and the silane coupling agent preferably being present in the aqueous solution in the mole ratio of between about 0.5:1.0 to about 3.0:1.0. In a preferred embodiment, the water soluble silane coupling agent is N-(2-aminoethyl)-3-aminopropyl-trimethoxysilane and the alkyltrialkoxysilane is methyltrimethoxysilane. In a most preferred embodiment, the methyltrimethoxysilane, the N-(2-aminoethyl)-3-aminopropyltrimethoxysilane, and the water are in an aqueous solution consisting of a weight percent ratio of 35.7:58.2:6.1. Therefore, the silicon-based aqueous solution comprising the present invention is selected from the group consisting of an aqueous solution of an alkali metal organosiliconate and an aqueous solution of a water soluble silane coupling agent and an alkyltrialkoxysilane.

The composition of the present invention can further include a second herbicide, an enhancer, or an adjuvant, which increases the activity or absorption of the first herbicide. In particular, the second herbicide is an acetanilide herbicide wherein the acetanilide herbicide increases the activity or absorption of the first herbicide in the composition. An example of an acetanilide herbicide is metolachlor or a mixture of the herbicide metolachlor and the safener benoxacor. In a preferred embodiment of the invention, the composition comprises an isoxazole herbicide such as isoxaflutole, an activator herbicide such as metolachlor, and the repellent adjuvant. In a more preferred embodiment of the invention, the composition comprises an isoxazole herbicide such as isoxaflutole, an activator herbicide such as metolachlor which is in combination with a safener such as benoxacor, and the repellent adjuvant.

The activity of certain herbicides can be increased by compounds that enhance absorption of the herbicide. Therefore, the present invention further includes compositions that comprise a herbicide, the repellent adjuvant, and an enhancer adjuvant which is an oil based adjuvant. In particular, the oil-based adjuvant is selected from the group consisting of a crop oil concentrate, a free fatty acid, and an esterified and saponified oil. Examples of herbicides that are known to work well in the presence of an oil-based adjuvant are the herbicides selected from the group consisting of cyclohexanidiones, aryloxyphenoxy, imidazolinone, and sulfonylurea herbicides.

The present invention also relates to a method for protecting cultivated plants including applying a herbicide formulation that has herbicidal activity from soil, the improvement comprising using as the herbicidal formulation a homogenous aqueous dispersion of the composition comprising a herbicide, and a repellent adjuvant for modifying the surface properties the composition so that retention of the composition on foliage of the cultivated plant is reduced. The herbicide in the method of the present invention is selected from the group consisting of acetanilides, acetamides, acetolactate synthase inhibitors, isoxazoles, diketonitriles, triketonitriles, dinitroanilines, triazines, substituted ureas, ethofumerates, isoxafen, oxodiazon, dithiopyr and combinations thereof. The repellent adjuvant is selected from the group consisting of an aqueous solution of an alkali metal organosiliconate and an aqueous solution of a water soluble silane coupling agent and an alkyltrialkoxysilane. In a preferred embodiment, the repellent adjuvant is selected from the group consisting of an aqueous solution of methyl siliconate and an aqueous solution of N-(2-aminoethyl)-3-aminopropyltrimethoxysilane and methyltrimethoxysilane. Optionally, the present invention can comprise a safener. In particular embodiments, the present invention optionally includes a safener selected from the group consisting of MON 4660, 2,2-dichloro-N,N-di-2-propenylacetamide, 3-dichloroacetyl-5-(2-furanyl)-2,2-dimethyl-oxazolidine, 2,2,5-trimethyl-N-dichloroacetyloxazolidine, 2,2-dimethyl-5-phenyl-N-dichloroacetyl oxazolidine, N,N-diallyl-2,2-dichloroacetamide, 2,2-dimethyl-5(2-furanyl)-N-dichloroacetyl oxazolidine, 2,2-dimethyl-5(2-thienyl)-N-dichloroacetyl oxazolidine, 2,2-spirocyclohexy-N-dichloroacetyl oxazolidine, 4-(dichloroacetyl)-3,4-dihydro-3-methyl-2H-1,4-benoxazine, 3-[3-(dichloroacetyl)-2,2-dimethyl-5-oxalidinyl]pyridine, 4-(dichloroacetyl)-1-oxa-4-azapiro-(4,5)-decane, 2,2-dichloro-1-(1,2,3,4-tetrahydro-1-methyl-2-isoquinolyl)ethanone, cis/trans-1,4-bis (dichloroacetyl)-2,5-dimethylpiperazine, N-(dichloroacetyl)-1,2,3,4-tetrahydroquinaldine, 1,5-bis(dichloroacetyl)-1,5-diazacyclononane, 1-(dichloroacetyl)-1-azaspiro[4,4] nonane, and combinations thereof.

The composition can further comprise an acetanilide herbicide as a second herbicide, which increases the activity or absorption of the first herbicide. In particular, the acetanilide herbicide in the composition can be metolachlor or a mixture of the herbicide metolachlor and the safener benoxacor. In a preferred embodiment of the invention the first herbicide comprising the composition is an isoxazole herbicide such as isoxaflutole.

The present invention further provides an improved method for protecting cultivated plants including the step of applying a herbicide compound, postemergence to the cultivated plants, the improvement which comprises adding a repellent adjuvant to the herbicide compound so that when the compound is applied to the cultivated plants, the compound bounces off foliage of cultivated plants to the soil. In the improved method, the repellent adjuvant is selected from any one of the repellent adjuvants disclosed herein. In the improved method, the herbicidal formulation can further comprise an enhancement material which enhances the activity of the herbicide. Enhancement materials can among other things include a second herbicide that activates or potentiates the activity of the first herbicide, or an oil-based adjuvant, or combinations of both. In a preferred embodiment, the herbicide is selected from the group consisting of acetanilides, acetamides, acetolactate synthase inhibitors, isoxazoles, diketonitriles, triketonitriles, dinitroanilines, triazines, substituted ureas, ethofumerates, isoxafen, oxodiazon, dithiopyr and combinations thereof. Optionally, the preferred method can include a safener. In particular embodiments, the present invention optionally includes a safener selected from the group consisting of MON 4660, 2,2-dichloro-N,N-di-2-propenylacetamide, 3-dichloroacetyl-5-(2-furanyl)-2,2-dimethyl-oxazolidine, 2,2,5-trimethyl-N-dichloroacetyloxazolidine, 2,2-dimethyl-5-phenyl-N-dichloroacetyl oxazolidine, N,N-diallyl-2,2-dichloroacetamide, 2,2-dimethyl-5(2-furanyl)-N-dichloroacetyl oxazolidine, 2,2-dimethyl-5(2-thienyl)-N-dichloroacetyl oxazolidine, 2,2-spirocyclohexy-N-dichloroacetyl oxazolidine, 4-(dichloroacetyl)-3,4-dihydro-3-methyl-2H-1,4-benoxazine, 3-[3-(dichloroacetyl)-2,2-dimethyl-5-oxalidinyl]pyridine, 4-(dichloroacetyl)-1-oxa-4-azapiro-(4,5)-decane, 2,2-dichloro-1-(1,2,3,4-tetrahydro-1-methyl-2-isoquinolyl)ethanone, cis/trans-1,4-bis (dichloroacetyl)-2,5-dimethylpiperazine, N-(dichloroacetyl)-1,2,3,4-tetrahydroquinaldine, 1,5-bis(dichloroacetyl)-1,5-diazacyclononane, 1-(dichloroacetyl)-1-azaspiro[4,4] nonane, and combinations thereof.

The present invention further provides a method for protecting cultivated plants without injuring cultivated plants, the steps comprising: (a) providing a herbicidal formulation comprising one or more herbicides admixed with a repellent adjuvant wherein the repellent adjuvant modifies the surface properties of the formulation thereby reducing retention of the formulation on foliage of the cultivated plants; (b) and applying the formulation to the cultivated plants wherein the formulation bounces off the foliage onto the soil wherein the formulation protects the cultivated plants without injuring the cultivated plants. In the method, the repellent adjuvant is any one of the repellent adjuvants disclosed herein. In the present invention, the herbicidal formulation can further comprise an enhancement material which enhances the activity of the herbicide. In particular embodiments of the present invention, the herbicide is selected from the group consisting of acetanilides, acetamides, acetolactate synthase inhibitors, isoxazoles, diketonitriles, triketonitriles, dinitroanilines, triazines, substituted ureas, ethofumerates, isoxafen, oxodiazon, dithiopyr and combinations thereof. Optionally, the present invention can comprise a safener. In particular embodiments, the present invention optionally comprises a safener selected from the group consisting of MON 4660, 2,2-dichloro-N,N-di-2-propenylacetamide, 3-dichloroacetyl-5-(2-furanyl)-2,2-dimethyl-oxazolidine, 2,2,5-trimethyl-N-dichloroacetyloxazolidine, 2,2-dimethyl-5-phenyl-N-dichloroacetyl oxazolidine, N,N-diallyl-2,2-dichloroacetamide, 2,2-dimethyl-5(2-furanyl)-N-dichloroacetyl oxazolidine, 2,2-dimethyl-5(2-thienyl)-N-dichloroacetyl oxazolidine, 2,2-spirocyclohexy-N-dichloroacetyl oxazolidine, 4-(dichloroacetyl)-3,4-dihydro-3-methyl-2H-1,4-benoxazine, 3-[3-(dichloroacetyl)-2,2-dimethyl-5-oxalidinyl]pyridine, 4-(dichloroacetyl)-1-oxa-4-azapiro-(4,5)-decane, 2,2-dichloro-1-(1,2,3,4-tetrahydro-1-methyl-2-isoquinolyl)ethanone, cis/trans-1,4-bis (dichloroacetyl)-2,5-dimethylpiperazine, N-(dichloroacetyl)-1,2,3,4-tetrahydroquinaldine, 1,5-bis(dichloroacetyl)-1,5-diazacyclononane, 1-(dichloroacetyl)-1-azaspiro[4,4] nonane, and combinations thereof.

The present invention further provides a method for inhibiting a weed without injuring turfgrass, the steps comprising (a) providing a liquid dispersion of a herbicidal formulation comprising one or more herbicides admixed with a repellent adjuvant wherein the repellent adjuvant modifies the surface properties of the formulation thereby reducing retention of the formulation on foliage of the turfgrass; and (b) applying the formulation to the crop plant wherein the formulation bounces off the foliage onto the soil wherein the formulation inhibits growth of the weed. In the method for protecting a turfgrass, the repellent adjuvant is any one of the repellent adjuvants disclosed herein. In the method, the herbicidal formulation can further comprise an enhancement material which enhances the activity of the herbicide. In particular embodiments of the method, the herbicide is selected from the group consisting of acetanilides, acetamides, acetolactate synthase inhibitors, isoxazoles, diketonitriles, triketonitriles, dinitroanilines, triazines, substituted ureas, ethofumerates, isoxafen, oxodiazon, dithiopyr and combinations thereof. Optionally, the present invention can comprise a safener. In particular embodiments, the present invention optionally includes a safener selected from the group consisting of 2,2-dichloro-N,N-di-2-propenylacetamide, 3-dichloroacetyl-5-(2-furanyl)-2,2-dimethyl-oxazolidine, 2,2,5-trimethyl-N-dichloroacetyloxazolidine, 2,2-dimethyl-5-phenyl-N-dichloroacetyl oxazolidine, N,N-diallyl-2,2-dichloroacetamide, 2,2-dimethyl-5(2-furanyl)-N-dichloroacetyl oxazolidine, 2,2-dimethyl-5(2-thienyl)-N-dichloroacetyl oxazolidine, 2,2-spirocyclohexy-N-dichloroacetyl oxazolidine, 4-(dichloroacetyl)-3,4-dihydro-3-methyl-2H-1,4-benoxazine, 3-[3-(dichloroacetyl)-2,2-dimethyl-5-oxalidinyl]pyridine, 4-(dichloroacetyl)-1-oxa-4-azapiro-(4,5)-decane, 2,2-dichloro-1-(1,2,3,4-tetrahydro-1-methyl-2-isoquinolyl)ethanone, cis/trans-1,4-bis (dichloroacetyl)-2,5-dimethylpiperazine, N-(dichloroacetyl)-1,2,3,4-tetrahydroquinaldine, 1,5-bis(dichloroacetyl)-1,5-diazacyclononane, 1-(dichloroacetyl)-1-azaspiro[4,4] nonane, and combinations thereof.

The amount of herbicide comprising the composition of the present invention and used in the method of the invention varies according to a number of parameters including the cultivated plant to be protected, the weed species to be controlled, and the edaphic and climatic conditions prevailing. In general, a rate of application from about 10 to 210 grams per hectare (g/ha) of herbicide is suitable, preferably 50 to about 158 g/ha. The rate of the repellent adjuvant in the composition can be from 0.25% to 1.0%, preferably at a rate of 0.5%.

According to general cultivation practices, herbicides are mixed in a tank and applied to the plants using a sprayer. The practitioner will mix various combinations of herbicides in the tank, and in some cases, will include a safener to ameliorate the herbicide's activity towards the plant to be protected. In practicing the present invention, the practitioner in addition to the mixture of herbicides, with or without a safener, in the tank will include the repellent adjuvant to make the composition of the present invention.

Cultivated plants within the meaning of the present invention includes any plant cultivated for food or ornamentation with the exception of weeds. The cultivated plants to be protected by the method of the present invention include crop plants of which corn, sugarcane, beans, rice, wheat, oats, sorghum, and a wide variety of vegetables such as tomatoes, and fruits such as strawberries are examples. In a preferred embodiment, the method of the invention is performed where the crop to be protected is corn (*Zea mays*), sorghum (*Sorghum halepense*), sorghum (*Sorghum bicolor*), soybean (*Glycine max*) or dry bean (*Phaseoulus vulgaris L.*). Examples of other cultivated plants that can be protected from a herbicide or combination of herbicides according to the present invention are turfgrasses; flowering garden plants such as roses, tulips, carnations, orchids and the like; various herb plants such as parsley, sage, rosemary, and thyme; ornamental plants such as shrubs, holly, juniper, and spice plants.

Thus, the objective of the present invention is to protect cultivated plants from injury from preemergence herbicides applied postemergence to the crop. Generally, these herbicides have activity from the soil, however it is not necessary that they have activity from the soil. The present invention results in decreased herbicide injury to the cultivated plant because it decreases foliar retention and adsorption of the herbicide by the cultivated plant. Prior to the present invention, the use of certain herbicide combinations as a postemergence application were precluded because the combination either caused injury to the cultivated plant, or caused injury to the cultivated plants because the cultivated plants were in a particularly sensitive stage at the time of the herbicide application. Therefore, many herbicide combinations cannot be used for a wide variety of cultivated plants. While the examples disclosed herein describe use of the present invention for postemergence herbicides, the present invention is not to be construed as being limited to postemergence herbicides. For example, it can be desirable to apply a preemergence pesticide to an existing turfgrass stand to kill germinating and emerging crabgrass seedlings. The present invention comprising a preemergence herbicide and a repellent adjuvant would direct the herbicide to the soil wherein the herbicide would be active.

In addition to soil activity, previous research has shown that isoxaflutole has foliar activity on a number of weed species (Sprague et al., Weed Sci. Soc. Amer. Abstr. 37: 5 (1997); Vrable et al., ibid.; and Young and Hart, Weed Sci. 46: 397–402 (1998)), possibly allowing for the use of postemergence applications of isoxaflutole for weed control. In fact, Sprague et al. (ibid.) reported that postemergence applications of isoxaflutole at 105 g/ha controlled common lambsquarters, common ragweed, redroot pigweed, and velvetleaf greater than 90% and when it was tank-mixed with metolachlor/benoxacor, the mixture controlled foxtail by greater than 80%. But this tank-mixture greatly reduced corn tolerance when it was applied after the corn had emerged. The basis for this corn injury was the result of increased isoxaflutole retention and subsequent absorption. This result indicated that metolachlor/benoxacor may act similar to various spray adjuvants that increase herbicide retention and thereby facilitating its subsequent absorption. Spray adjuvants are normally added to foliar-applied herbicide spray solutions to maximize the effectiveness of the herbicide. These adjuvants usually exert this enhancing effect by increasing herbicide spray retention on the leaf surface and by increasing herbicide penetration into the plant cuticle. A major barrier in the retention of a herbicide is the surface tension of the spray droplets. Adjuvants such as non-ionic surfactants (NIS) and 28% urea ammonium nitrate (UAN) have been found to decrease the surface tension of spray droplets, which results in an increase in surface coverage of the spray solution (De Ruiter et al., Weed Sci. 38: 567–572 (1990); Stevens et al., Pestic. Sci. 38: 237–245 (1993)). However, there are apparently no adjuvants which can be used to modify the surface properties of a herbicide solution, which in turn decreases herbicide retention and, therefore, the herbicide absorption. The present invention provides herbicide mixtures containing adjuvants which function as repellent adjuvants because they modify the surface properties of the mixtures. It is theorized that the repellent adjuvants modify the surface property of the mixture by causing an increase in the surface tension of the mixture, which results in spray droplets of increased surface tension. Because of the increased surface tension, the herbicide spray droplets are not retained by the plant foliage. Thus, the present invention permits the postemergence application of the herbicide mixtures disclosed herein.

The herbicide isoxaflutole by itself is not injurious to corn when applied preemergence to the corn. However, when isoxaflutole is applied to corn postemergence it causes injury to the corn. The injury is particularly severe when isoxaflutole is combined with metolachlor and benoxacor, and the combination is applied to corn plants in the spike, 2-leaf, or 4-leaf stage. The reason is that the metolachlor or any other acetanilide herbicide applied with isoxaflutole increases spray retention on the corn leaves, which ultimately increases the absorption of isoxaflutole or any other isoxazole by the corn plant. For example, DUAL II is an oily composition which when mixed with the herbicide forms a composition that facilitates absorption of the herbicide by the leaf. It is the increased absorption of the isoxazole herbicide that causes the injury to corn. Therefore, when acetanilide herbicides are used in combination with other herbicides, the acetanilide herbicide may increase the retention and absorption of the other herbicide by the plant. Herbicide absorption can also be enhanced when in combination with oil-based adjuvants such as crop oil concentrate, free fatty acids, and esterified and saponified oils. Examples of such herbicides whose absorption is enhanced by oil-based adjuvants are cyclohexanidiones, aryloxyphenoxy, imidazolinone, and sulfonylurea herbicides.

The present invention is an improvement because it involves including in the herbicide spray solution, a material that modifies the surface properties of the spray solution, which results in decreased adherence of the spray droplets to the plant leaves. This is particularly useful when the plant is at a vulnerable stage of growth. For example, a crop such as dry beans can be at a sensitive growth stage (unifolate) at the time it is most desirable to apply an acetanilide herbicide such as dimethamid. The present invention decreases foliar absorption of the herbicide by the bean leaves, yet allows the herbicide to exert its action from the herbicide that has reached the soil.

Therefore, the present invention is a herbicide and water repellent composition wherein the surface properties of the composition is modified by the water repellent compound therein. Because these materials modify the surface properties of the herbicide spray solution, the spray droplets form spheres which bounce off the plant foliage. The water repellent compounds suitable for modifying the surface properties to make the herbicide composition of the present invention include an aqueous solution of an organosiliconate and aqueous siloxane solutions. An example of an aqueous solution of an organosiliconate that modifies the surface properties of the herbicide spray composition is an aqueous solution of sodium methyl siliconate. Sodium methyl siliconate has been used as a water repellent treatment for surfaces (see U.S. Pat. No. 5,780,412 to Scarbourgh and references therein). An example of an aqueous siloxane solution that is suitable is an aqueous solution of a water soluble silane coupling agent and an alkyltrialkoxysilane that modifies the surface properties of the herbicide spray composition such as an aqueous solution of N-(2-aminoethyl)-3-aminopropyltrimethoxysilane and methyltrimethoxysilane. When these compounds are mixed with an aqueous solution, they form an emulsion. Siloxanes are described in U.S. Pat. No. 3,294,725 to Findlay et al. which is hereby incorporated herein by reference and aqueous solutions consisting of water soluble silane coupling agents and alkyltrialkoxysilanes are described in U.S. Pat. Nos. 5,051,129 and 5,073,195, both to Cuthbert et al. which are hereby incorporated herein by reference to teach compositions which are suitable as repellent adjuvants in the present invention and methods for making them. While it may appear that any silicone containing compound may be suitable for making the compositions of the present invention, the inventors have discovered otherwise. For example, methyltrimethoxysilane and a phosphonate ester alkyl silicon are water soluble silicon compounds. However, neither of these compounds is effective at producing a composition according to the present invention.

In an embodiment of the present invention disclosed herein, the herbicidal composition comprises isoxaflutole (5-cyclopropyl isoxazol-4-4-yl-2-mesyl-trifluoromethylphenyl ketone); a mixture of the herbicide metolachlor (2-chloro-N-(2-ethyl-6-methylphenyl)-N-(2-methoxy-1-methylethyl)acetamide) or acetochlor, and the safener benoxacor ((4-dichloroacetyl)-3,4-dihydro-3-methyl-2H-1,4-benoxazine), MON 13900 or dichlormid; and any one of the repellent adjuvants disclosed herein. In a preferred embodiment, the herbicidal composition comprises the isoxaflutole as BALANCE, the metolachlor and benoxacor mixture as DUAL II, and the repellent adjuvant selected from the group consisting of an aqueous solution of sodium methyl siliconate and an aqueous solution of N-(2-aminoethyl)-3-aminopropyl-trimethoxysilane.

While the examples disclosed herein relate to the herbicide isoxaflutole, the present invention is not to be construed as being limited to the herbicide isoxaflutole. Examples of other herbicides which are encompassed by the present invention are nicosulfron which is 2-[[[[(4,6-dimethoxy-2-pyrimidinyl)amino]carbonyl]amino]sulfonyl]-N,N-dimethyl-3-pyridinecarboxamide—(ACCENT, Dupont, Wilmington, Del.; isopropylamine salt, glyphosphate with adjuvants, (ACCORD, Monsanto Company, St. Louis, Mo.); primisulfuron which is methyl 2-[[[[[4,6-bis (difluoromethoxy)-2-pyrimidinyl]amino]carbonyl]amino] sulfonyl]benzoate (BEACON, Novartis, Greensboro, N.C.); Chlorimuron which is ethyl-2-[[[[(4-chloro-6-methoxy-2-pyrimidinyl)amino]carbonyl]amino]sulfonyl]benzoate ethyl (CLASSIC, Du Pont, Wilmington, Del.); Glufosinate-ammonium salt which is (2-amino-4-(hydroxymethylphosphinyl)butanoic acid (LIBERTY, AgrEvo, Wilmington, Del.); Linuron which is N1-(3,4-dichlorophenyl)-N-methoxy-N-methylurea) (LOROX, Bayer, Kansas City, Kans.); Linuron and chlorimuron ethyl (LOROX PLUS, Dupont, Wilmington, Del.); Thifensulfuron which is (methyl 3-[[[[(4-methoxy-6-methyl-1,3,5-triazin-2-yl]carbonyl]amino]sulfonyl]-2-thiophenecarboxylate)(PINNACLE, Dupont, Wilmington, Del.); Imazethapyr (PURSUIT, American Cyanamid, Princeton, N.J.); glyphosate-isopropyl amine salt which is (N-(phosphonomethyl)glycine) (ROUNDUP, Monsanto Company, St. Louis, Mo.); ROUNDUP with surface components (phosphate esters and cationic tallow amines (ROUNDUP ULTRA, Monsanto Company, St. Louis, Mo.); imazaquin which is (2-[4,5-dihydro-4-methyl-4-(1-methylethyl)-5-oxo-1H-imidazol-2-yl]-3-quinoline carboxylic acid) (SCEPTER, American Cyanamid, Princeton, N.J.); acetochlor which is HARNESS and SURPASS (available from Monsanto Company, and Zeneca Ag-Products Wilmington, Del., respectively); alachlor, which is 2-chloro-2',6'-diethyl-N-(methoxymethyl) acetanilide and sold as LASSO (available from Monsanto Company); EPTC which is S-ethyl dipropylthiocarbonate and sold as ERADICANE (available from Zeneca Ag-Products); halosulfuron which is PERMIT and BATTALION (available from Monsanto company); EPIC which is isoxaflutole, and flufenacet (BAYFOE 5043) which is 4-fluoro-N-isopropyl-2-[[5-trifluoromethyl)-1,3,4-thiadiazol-2yl]oxy]acetamide (available from Bayer); and glyphosphate-trimethylsulfonium salt (N-(phosphonomethyl)glycine) (TOUCHDOWN, Zeneca Ag-Products).

In addition to the composition of the present invention containing a herbicide and the repellent adjuvant, the present invention can further comprise activators, enhancers and safeners. Therefore, the present invention can further comprise a monosaccharide wherein the monosaccharide acts as an enhancer or potentiator for the herbicide in killing the weed without decreasing tolerance of the crop to the herbicide. Examples of such compositions are in U.S. application Ser. No. 08/984,407 filed Dec. 3, 1997 which is herein incorporated by reference. The present invention can further include oil-based adjuvants such as crop oil concentrate, free fatty acids, and esterified and saponified oils. The present invention can further include a safener which causes a reduction in injury to the crop plant without an unacceptable reduction in the herbicidal action. Examples of safeners encompassed by the present invention include benoxacor which is (4-dichloroacetyl)-3,4-dihydro-3-methyl-2H-1,4-benoxazine; dichlormid which is 2,2-dichloro-N,N-di-2-propenylacetamide (available from Zeneca, Inc.); MON 4660 which is available from Monsanto Company; R-29148 which is 2,2,5-trimethyl-N-dichloroacetyloxazolidine (available from Zeneca Ag-Products); R-25788 which is N,N-diallyl-2,2-dichloroacetamide (available from Zeneca Ag-Products); and MON 13900 which is 3-dichloroacetyl-5-(2-furanyl)-2,2-dimethyl-oxazolidine (available from Monsanto Company). Other safeners include 2,2-dimethyl-5-phenyl-N-dichloroacetyl oxazolidine, 2,2-dimethyl-5(2-furanyl)-N-dichloroacetyl oxazolidine, 2,2-dimethyl-5(2-thienyl)-N-dichloroacetyl oxazolidine, 2,2-spirocyclohexy-N-dichloroacetyl oxazolidine, 4-(dichloroacetyl) -3,4-dihydro-3-methyl-2H-1,4-benoxazine, 3-[3-(dichloroacetyl)-2,2-dimethyl-5-oxalidinyl]pyridine, 4-(dichloroacetyl)-1-oxa-4-azapiro-(4,5)-decane, 2,2-dichloro-1-(1,2,3,4-tetrahydro-1-methyl-2-isoquinolyl) ethanone, cis/trans-1,4-bis(dichloroacetyl)-2,5-dimethylpiperazine, N-(dichloroacetyl)-1,2,3,4-tetrahydroquinaldine, 1,5-bis(dichloroacetyl)-1,5-diazacyclononane, 1-(dichloroacetyl)-1-azaspiro[4,4] nonane, and combinations thereof. Safeners are also disclosed in U.S. Pat. No. 5,627,131 to Shribbs et al. which is hereby incorporated herein by reference. Examples of particular herbicide and safener combinations include DUAL II which consists of metolachlor and benoxacor (available from Novartis); SURPASS which consists of acetochlor and dichlormid (available from Zeneca Ag-Products); MON 8407 which consists of acetochlor and MON 4660 (available from Monsanto Company); ERADICANE which consists of EPTC and R-29148 (available from Zeneca Ag-Products); BATTALION which consists of a halosulfuron and MON 13900 (available from Monsanto Company); and MON 8411 which consists of acetochlor and MON 13900 (available from Monsanto Company). A particularly desirable combination of herbicide and safener is the herbicide acetochlor mixed with a safener selected from the group consisting of dichlormid, MON-13900 (flurilazole), R-29148, R-25788 (dichlormid), MON 4660 and combinations thereof.

The following examples are intended to promote a further understanding of the present invention.

EXAMPLE 1

Various silicone-based compounds were evaluated for ability to prevent herbicidal injury to the corn when used as repellent adjuvants in herbicide formulations. In previous experiments, it was shown that isoxaflutole in combination with metolachlor and benoxacor applied once corn had emerged caused significant corn injury. The basis of this severe injury is the retention and subsequent absorption of isoxaflutole in the foliar tissue of the corn plant, which is exacerbated by the metolachlor herbicide in the composition. Therefore, to address this problem, a number of silicon-based compounds, which were believed to have repellent properties, were evaluated for the ability to prevent injury to corn plants. The compounds evaluated were an aqueous solution of 32 weight percent sodium methyl siliconate and 67 weight percent water ("SMS"), an aqueous solution of 35.7 weight percent N-(2-aminoethyl)-3-aminopropyltrimethoxysilane, 58.2 weight percent methyltrimethoxysilane, and 6.1 weight percent water ("AFS-MTMS"), methyltrimethoxysilane ("MTMS"), and phosphonate ester alkyl silicon ("PEAS"). These test adjuvants are commercially available from Dow Corning, Midland, Mich. The test adjuvants were applied in combination with isoxaflutole or isoxaflutole in combination with metolachlor and the safener benoxacor, and the ability of the combination to reduce plant injury by inhibiting retention and subsequent absorption of the herbicide was evaluated.

Pioneer 3573 corn seeds (Pioneer 3573, a product of Pioneer Hi-Bred International, Inc., Des Moines, Iowa) were planted 2.54 cm deep, and velvetleaf and barnyardgrass seeds were planted 1.0 cm deep in 875 ml pots containing BACCTO professional greenhouse potting mix (a product of Michigan Peat Co., Houston, Tex.). The seedlings were grown in a greenhouse maintained at 25° C.±2° C. Natural sunlight was supplemented with light from sodium vapor lamps, which provided a total midday light intensity of 1,000 $\mu$mol $m^{-2}$ $s^{-1}$ photosynthetic photon flux at plant height during a 16 hour photoperiod. Plants were watered daily and fertilized weekly with 50 ml of a water soluble fertilizer solution (400 ppm nitrogen, 400 ppm $P_2O_5$, and 400 ppm $K_2O$).

Isoxaflutole was combined with three different rates (0.25%, 0.5%, and 1.0%) of the four test adjuvants, which were then applied to postemergence to 2-leaf (5 inch) corn plants. Generally, corn leaf stages are described as the number of visible leaves. Isoxaflutole at 105 g/ha and isoxaflutole tank-mixed with 1.1 kg/ha of metolachlor/benoxacor were applied either alone or in combination with ACTIVATOR 90, a non-ionic surfactant (NIS) product of Loveland Industries Inc., Greeley, Colo.) at 0.25% (v/v). The various herbicide applications were made to corn at the 2-leaf (V1) growth stage.

The herbicide compositions were applied through an 8003 E flat fan nozzle (available from Spraying Systems Co., Wheaton, Ill.) delivering 234 L/ha at a pressure of 172 kPa (25 gallons/acre). Corn tolerance was evaluated 8 days after treatment (DAT) by visually evaluating the plants for bleaching and necrotic symptoms and also by measuring corn height (base of the plant to its crown). Visual corn injury ratings were based on a scale from 0 to 100, with 0 indicating no effect and 100 indicating plant death. Corn height was measured in cm and presented as a percent of the non-treated plants, with 0 indicating total reduction in plant height and 100 indicating height equal to the non-treated plants. All experiments were conducted twice as completely randomized designs with four replications. Data were subjected to analysis of variance and means separated using Fisher's Protected LSD test at $\alpha$=0.05. Statistical analysis indicated no experimental run interactions, so the data were combined and reported as the means of two experiments. Non transformed means are presented since arcsine and square root transformations did not alter the interpretation of the data.

The data for the experiments are presented in Tables 1 and 2, which show that isoxaflutole when applied to corn by itself did not significantly injure the corn. But when isoxaflutole was applied in combination with metolachlor/benoxacor, severe corn injury of 47% occurred and plant height was reduced by 48%. However, when the mixture of isoxaflutole and metolachlor/benoxacor was mixed with either SMS or AFS-MTMS, this injury was reduced to less than 10%. In contrast, neither of the other silicon-based compounds, MTMS or PEAS, reduced injury to corn when added to the isoxaflutole or isoxaflutole and metolachlor/benoxacor mixture. It is interesting that the other silicon-based compositions were not effective in ameliorating the herbicide's affect on the corn, in particular MTMS. Therefore, this example shows that only the adjuvants, SMS and AFS-MTMS, decreased the retention and subsequent absorption of isoxaflutole when either adjuvant was in combination with metolachlor/benoxacor.

TABLE 1

Isoxaflutole Injury to Corn in Greenhouse Trials

| Treatment | Adjuvant Rates 0% | 0.25% | 0.5% | 1.0% |
|---|---|---|---|---|
| | -(% injury to corn)- | | | |
| Isoxaflutole | 2 | | | |
| Isoxaflutole + Activator 90 | | 15 | | |
| Isoxaflutole + PEAS | | 2 | 0 | 0 |
| Isoxaflutole + SMS | | 0 | 0 | 0 |
| Isoxaflutole + AFS-MTMS | | 0 | 0 | 0 |
| Isoxaflutole + MTMS | | 1 | 0 | 0 |
| Isoxaflutole + Metolachlor[a] | 47 | | | |
| Isoxaflutole + Metolachlor + Activator 90 | | 59 | | |
| Isoxaflutole + Metolachlor + PEAS | | 52 | 49 | 51 |
| Isoxaflutole + Metolachlor + SMS | | 8 | 9 | 7 |
| Isoxaflutole + Metolachlor + AFS-MTMS | | 8 | 3 | 2 |
| Isoxaflutole + Metolachlor + MTMS | | 51 | 56 | 56 |

[a]The formulation metolachlor contained the herbicide safener benoxacor.

TABLE 2

| Corn Height as a Percent of Control, 8 DAT in Green House Trials | | | | |
|---|---|---|---|---|
| | Adjuvant Rates | | | |
| Treatment | 0% | 0.25% | 0.5% | 1.0% |
| | -(% of control height)- | | | |
| Isoxaflutole | 100 | | | |
| Isoxaflutole + Activator 90 | | 96 | | |
| Isoxaflutole + PEAS | | 107 | 110 | 107 |
| Isoxaflutole + SMS | | 107 | 107 | 110 |
| Isoxaflutole + AFS-MTMS | | 107 | 107 | 114 |
| Isoxaflutole + MTMS | | 103 | 110 | 107 |
| Isoxaflutole + Metolachlor[a] | 62 | | | |
| Isoxaflutole + Metolachlor + Activator 90 | | 66 | | |
| Isoxaflutole + Metolachlor + PEAS | | 62 | 69 | 69 |
| Isoxaflutole + Metolachlor + SMS | | 100 | 100 | 100 |
| Isoxaflutole + Metolachlor + AFS-MTMS | | 107 | 107 | 103 |
| Isoxaflutole + Metolachlor + MTMS | | 69 | 62 | 66 |

[a]The formulation metolachlor contained the herbicide safener benoxacor.

The results of Tables 1 and 2 for the various herbicide mixtures containing adjuvants added at a rate of 0. 5% are presented in Table 3. Table 3 shows that injury to 2-leaf corn by isoxaflutole was reduced to 0 only when SMS or AFS-MTMS was mixed with the herbicide. The table further shows that injury to corn caused by isoxaflutole in combination with metolachlor/benoxacor was reduced from 47% to 8% and 3% by SMS and AFS-MTMS, respectively. The table also shows that isoxaflutole in combination with metolachlor/benoxacor reduced corn height by about 40% whereas adding either SMS or AFS-MTMS to the composition completely abrogated any affect the composition had on corn growth. The table clearly shows that the silicon-based compositions, PEAS and MTMS, were not useful as repellent adjuvants in herbicidal compositions. Therefore, this example demonstrates the present invention comprising either SMS or AFS-MTMS reduces herbicidal injury to corn when applied postemergence.

TABLE 3

| | | Injury[b] | | Height | |
|---|---|---|---|---|---|
| Treatment[a] | Rate | Isoxaflutole[c] | Isoxaflutole + metolachlor[d] | Isoxaflutole | Isoxaflutole + metolachlor[d] |
| | | -%- | | -% of control- | |
| Alone | 0.25% v/v | 2 | 47 | 100 | 64 |
| +NIS | 0.5% v/v | 15 | 59 | 98 | 65 |
| +PEAS | 0.5% v/v | 0 | 49 | 110 | 69 |
| +SMS | 0.5% v/v | 0 | 8 | 106 | 99 |

TABLE 3-continued

| | | Injury[b] | | Height | |
|---|---|---|---|---|---|
| Treatment[a] | Rate | Isoxaflutole[c] | Isoxaflutole + metolachlor[d] | Isoxaflutole | Isoxaflutole + metolachlor[d] |
| +AFS-MTMS | 0.5% v/v | 0 | 3 | 107 | 105 |
| +MTMS | 0.5% v/v | 0 | 56 | 108 | 62 |
| $LSD_{0.05}$ | | | -4- | | -8- |

[a]Treatments were applied to 2-leaf (12) corn.
[b]Visual injury ratings and corn heights were evaluated 8 DAT.
[c]Isoxaflutole was applied at 105 g/ha.
[d]The formulation of metolachlor contained the herbicide safener benoxacor and was applied at 1.1 kg/ha.

EXAMPLE 2

The greenhouse experiments showed that adding SMS or AFS-MTMS to a herbicide mixture rendered the herbicide safe for use on cultivated plants without reducing the herbicide's effective against weeds. However, greenhouse experiments are performed under controlled conditions. Therefore, field experiments were performed to assess how the present invention would perform under actual farm conditions.

Conventional tillage experiments were conducted in 1998 to evaluate the influence of SMS and AFS-MTMS, on corn tolerance and weed control from postemergence applications of isoxaflutole alone and in tank-mixture with metolachlor/benoxacor. Experiments were conducted at the Michigan State University Crop and Soil Science Research Farm at East Lansing, Mich. on Capac sandy clay loam soil (fine-loamy, mixed mesic Acric Ochraqualfs) containing 3.1% organic matter with a pH of 6.3 in 1998.

Tillage consisted of moldboard plowing in the fall prior to spring disking and field cultivation. Prior to spring cultivation, 320 kg/ha of 46-0-0 fertilizer was applied broadcast. At planting, 140 kg/ha of 6-24-24 fertilizer was applied as a banded treatment 5 cm below and 5 cm beside the corn seeds. Pioneer 37R71 corn was planted on May 11, 1998 at a rate of 62,000 seeds/ha. Each plot was 10.6 m long and consisted of 4 rows spaced 76 cm apart.

The tillage experiments were conducted as a randomized complete block design in a factorial arrangement with three replications. The factors consisted of herbicide application timing and herbicide treatment. Herbicides were applied when the corn was at the 2-leaf and 4-leaf stages. Corn leaf stages are described as the number of visible leaves. Herbicide treatments included isoxaflutole alone (BALANCE) at 105 g/ha and in combination with 1.1 kg/ha of metolachlor/benoxacor (DUAL II). Each of these treatments were applied either alone or with either SMS or AFS-MTMS. Each repellent was used at a rate of 0.5% v/v. Additional treatments not included in the factorial arrangement were an untreated check and a weed-free check. All herbicides were applied with a tractor mounted, compressed-air sprayer calibrated to deliver 2.6 L/ha at 207 kPa using 8003 E flat-fan nozzles.

Corn tolerance was evaluated 30 days after planting (DAP) by visually evaluating plants for bleaching and necrotic symptoms and also by measuring corn height (base of plant to the crown) 40 DAP. Weed control by species was visually evaluated 60 DAP. Visual evaluations were based on a scale of 0 (no effect) to 100% (complete weed or crop death). Corn grain yield was determined by harvesting the center two rows of each plot with a plot combine. Seed weight was adjusted to 15% moisture.

Data were subjected to analysis of variance and means separated using Fisher's Protected LSD test at $\alpha$=0.05. Data were combined over years when treatment and/or application timing by year interactions were not significant $\alpha$=0.05. Non-transformed means for corn injury and weed control are presented since arcsine and square root transformations did not alter the interpretation of the data. Corn height and yield results were converted to a percent of the weed-free treatment after separation.

Herbicide application times, corn stages, weed heights, and densities for the field trial in 1998 are presented in Table 4 and rainfall data in Table 5.

TABLE 4

| | 1998 | |
|---|---|---|
| | 2-Leaf[a] | 4-Leaf |
| Days after planting[b] | 9 | 15 |
| Corn | | |
| Leaves with collars | 1 | 2 |
| Ave. height (cm) | 10 | 13 |
| Giant foxtail | | |
| Ave. height (cm) | 0.6 | 4 |
| Density (plants/$m^2$) | 33 | 65 |
| Broadleaf weeds[c] | | |
| Ave. height | 0.6 | 3 |
| Ave. density (plants/$m^2$) | 44 | 44 |

[a]Corn leaf stage refers to the number of visible leaves.
[b]Corn planted May 11, 1998.
[c]Broadleaf weeds include: common lambsquarters, redroot pigweed, common ragweed, and velvetleaf.

TABLE 5

| Days after planting | Amount of Rainfall 1998 |
|---|---|
| | -mm- |
| 0–7 | 2 |
| 8–14 | 3 |
| 15–21 | 12 |
| 22–28 | 0 |
| Total | 17 |

Corn (ZEAMX) in the 2-leaf or 4-leaf stage was treated with herbicidal compositions consisting of BALANCE (isoxaflutole); BALANCE and DUAL II (metolachlor and the safener benoxacor); BALANCE and SMS; BALANCE and AFS-MTMS; BALANCE, DUAL II and SMS; or BALANCE, DUAL, and AFS-MTMS. The percent injury was determined 6 DAT, 12 DAT, and 30 DAP. As weed controls, the annual grasses (ANGR) and common lambsquarters, *Chenopodium album L.* (CHEAL) were treated with herbicidal compositions consisting of BALANCE; BALANCE and DUAL II; BALANCE and SMS; BALANCE and AFS-MTMS; BALANCE, DUAL II and SMS; or BALANCE, DUAL, and AFS-MTMS. The percent injury for the weed controls was determined 30 DAP.

The results are shown in Table 6. The results show that the repellent adjuvants SMS and AFS-MTMS were effective in reducing the percent injury to corn caused by the herbicide when either was included in herbicidal compositions consisting of BALANCE and DUAL II. AFS-MTMS was particularly effective, when it was included in the herbicidal composition and applied to 2-leaf corn plants, corn injury 6 DAT was only 7.3%, whereas without AFS-MTMS, the corn injury was 65%. By 12 DAT and beyond, corn injury of caused by the BALANCE and DUAL II composition containing AFS-MTMS was not detectable whereas without AFS-MTMS, the injury remained about 55–50%. The weed controls show that SMS and AFS-MTMS do not appear to reduce the efficacy of BALANCE and DUAL II to control weeds.

The results in Table 6 also show that SMS and AFS-MTMS reduced injury to corn at the 4-leaf stage when included in herbicidal compositions containing both BALANCE and DUAL II. In particular, the percent injury to corn was significantly reduced when the herbicidal composition included AFS-MTMS as the repellent adjuvant. The results further show that including a safener in the herbicide composition (the benoxacor) had no safening effect when used in combination with isoxaflutole. These results demonstrate that the present invention is useful and effective under actual field conditions.

TABLE 6

| | | | | | Weed Code: | | | | ANGR | CHEAL |
|---|---|---|---|---|---|---|---|---|---|---|
| | | | | | Crop Code: | | ZEAMX | | | |
| | | Treatment/Evaluation Interval | | | | 6 DAT | 12 DAT | 30 DAP | 30 DAP | 30 DAP |
| | | Date evaluated | | | | May 26, 1998 | Jun. 1, 1998 | Jun. 1, 1998 | Jun. 1, 1998 | Jun. 1, 1998 |
| No. | Composition | Form Amt | Rate | Rate Unit | Grow Stg | | Injury Percent | | Control Percent | |
| 1 | BALANCE | 75 | 1.5 | OZ A/A | 2-leaf | 0.0 | 0.0 | 0.0 | 41.7 | 98.3 |
| 2 | BALANCE | 75 | 1.5 | OZ A/A | 2-leaf | 0.0 | 0.0 | 0.0 | 50.0 | 100.0 |
| | SMS | | 0.5 | % V/V | | | | | | |
| 3 | BALANCE | 75 | 1.5 | OZ A/A | 2-leaf | 0.0 | 0.0 | 0.0 | 35.0 | 97.3 |
| | AFS-MTMS | | 0.5 | % V/V | | | | | | |
| 4 | BALANCE | 75 | 1.5 | OZ A/A | 2-leaf | 65.0 | 55.0 | 50.0 | 99.3 | 100.0 |
| | DUAL II | 7.8 | | LB A/A | | | | | | |
| 5 | BALANCE | 75 | 1.5 | OZ A/A | 2-leaf | 23.3 | 5.0 | 5.7 | 96.0 | 100.0 |
| | DUAL II | 7.8 | 1.0 | LB A/A | | | | | | |
| | SMS | | 0.5 | % V/V | | | | | | |
| 6 | BALANCE | 75 | 1.5 | OZ A/A | 2-leaf | 7.3 | 0.0 | 0.0 | 98.7 | 100.0 |
| | DUAL II | 7.8 | 1.0 | LB A/A | | | | | | |
| | AFS-MTMS | | 0.5 | % V/V | | | | | | |
| 7 | BALANCE | 75 | 1.5 | OZ A/A | 4-leaf | | 16.7 | 9.7 | 48.3 | 100.0 |

TABLE 6-continued

| | | | | | Weed Code: | | | | ANGR | CHEAL |
|---|---|---|---|---|---|---|---|---|---|---|
| | | | | | Crop Code: | | ZEAMX | | | |
| | | Treatment/Evaluation Interval | | | | 6 DAT | 12 DAT | 30 DAP | 30 DAP | 30 DAP |
| | | | Date evaluated | | | May 26, 1998 | Jun. 1, 1998 | Jun. 1, 1998 | Jun. 1, 1998 | Jun. 1, 1998 |
| No. | Composition | Form Amt | Rate | Rate Unit | Grow Stg | | Injury Percent | | Control Percent | |
| 8 | BALANCE | 75 | 1.5 | OZ A/A | 4-leaf | | 15.0 | 10.7 | 41.7 | 100.0 |
| | SMS | | 0.5 | % V/V | | | | | | |
| 9 | BALANCE | 75 | 1.5 | OZ A/A | 4-leaf | | 10.0 | 10.0 | 55.0 | 48.3 |
| | AFS-MTMS | | 0.5 | % V/V | | | | | | |
| 10 | BALANCE | 75 | 1.5 | OZ A/A | 4-leaf | | 81.7 | 83.3 | 100.0 | 100.0 |
| | DUAL II | 7.8 | 1.0 | LB A/A | | | | | | |
| 11 | BALANCE | 75 | 1.5 | OZ A/A | 4-leaf | | 48.3 | 30.0 | 100.0 | 99.3 |
| | DUAL II | 7.8 | 1.0 | LB A/A | | | | | | |
| | SMS | | 0.5 | % V/V | | | | | | |
| 12 | BALANCE | 75 | 1.5 | OZ A/A | 4-leaf | | 26.7 | 16.7 | 98.7 | 99.7 |
| | DUAL II | 7.8 | 1.0 | LB A/A | | | | | | |
| | AFS-MTMS | | 0.5 | % V/V | | | | | | |
| 13 | Untreated | | | | | | 0.0 | 0.0 | 0.0 | 0.0 |
| LSD (P = 0.05) | | | | | | 4.65 | 7.99 | 7.52 | 14.50 | 15.82 |
| Standard Deviation | | | | | | 2.61 | 4.74 | 4.46 | 8.61 | 9.39 |
| CV | | | | | | 19.11 | 23.87 | 26.86 | 12.94 | 10.68 |

BALANCE - isoxaflutole;
DUAL II - metolachlor/benoxacor;
DAT—day after treatment;
DAP—day after planting;
ZEAMX - corn, *Zea mays* L.;
ANGR - annual grasses_;
CHEAL - common lambsquarter, *Chenopodium album* L.

Additional weed controls consisted of the weeds giant foxtail, *Setaria faberi Herrm.* (SETFA); redroot pigweed, *Amaranthus retroflexus L.* (AMARE); common ragweed, *Ambrosia artemisiifolia* (AMBEL); and velvetleaf, *Abutilon theophrasti medicus* (ABUTH). The weed controls were treated as above with herbicidal compositions consisting of BALANCE; BALANCE and DUAL II; BALANCE and SMS; BALANCE and AFS-MTMS; BALANCE, DUAL II and SMS; or BALANCE, DUAL, and AFS-MTMS. As shown in Table 7, there was no significant difference in herbicidal efficacy between herbicidal compositions that contained either the SMS or AFS-MTMS repellent adjuvant and herbicidal compositions that did not contain either repellent adjuvant.

TABLE 7

| | | | | | Weed Code: | AMARE | AMBEL | ABUTH |
|---|---|---|---|---|---|---|---|---|
| | | Treatment/Evaluation Interval | | | | 30 DAP | 30 DAP | 30 DAP |
| | | | Date evaluated | | | Jun, 9, 1998 | Jun, 9, 1998 | Jun, 9, 1998 |
| No. | Composition | Form Amt | Rate | Unit | Grow Stg | | Control Percent | |
| 1 | BALANCE | 75 | 1.5 | OZ A/A | 2-leaf | 100.0 | 100.0 | 98.3 |
| 2 | BALANCE | 75 | 1.5 | OZ A/A | 2-leaf | 100.0 | 100.0 | 99.3 |
| | SMS | | 0.5 | % V/V | | | | |
| 3 | BALANCE | 75 | 1.5 | OZ A/A | 2-leaf | 95.0 | 100.0 | 100.0 |
| | AFS-MTMS | | 0.5 | % V/V | | | | |
| 4 | BALANCE | 75 | 1.5 | OZ A/A | 2-leaf | 100.0 | 100.0 | 100.0 |
| | DUAL II | 7.8 | | LB A/A | | | | |
| 5 | BALANCE | 75 | 1.5 | OZ A/A | 2-leaf | 100.0 | 100.0 | 97.7 |
| | DUAL II | 7.8 | 1.0 | LB A/A | | | | |
| | SMS | | 0.5 | % V/V | | | | |
| 6 | BALANCE | 75 | 1.5 | OZ A/A | 2-leaf | 100.0 | 100.0 | 99.3 |
| | DUAL II | 7.8 | 1.0 | LB A/A | | | | |
| | AFS-MTMS | | 0.5 | % V/V | | | | |
| 7 | BALANCE | 75 | 1.5 | OZ A/A | 4-leaf | 100.0 | 100.0 | 95.7 |
| 8 | BALANCE | 75 | 1.5 | OZ A/A | 4-leaf | 100.0 | 100.0 | 97.0 |
| | SMS | | 0.5 | % V/V | | | | |
| 9 | BALANCE | 75 | 1.5 | OZ A/A | 4-leaf | 98.3 | 97.3 | 95.7 |
| | AFS-MTMS | | 0.5 | % V/V | | | | |
| 10 | BALANCE | 75 | 1.5 | OZ A/A | 4-leaf | 100.0 | 100.0 | 98.3 |
| | DUAL II | 7.8 | 1.0 | LB A/A | | | | |
| 11 | BALANCE | 75 | 1.5 | OZ A/A | 4-leaf | 100.0 | 100.0 | 97.0 |
| | DUAL II | 7.8 | 1.0 | LB A/A | | | | |
| | SMS | | 0.5 | % V/V | | | | |
| 12 | BALANCE | 75 | 1.5 | OZ A/A | 4-leaf | 100.0 | 100.0 | 98.3 |
| | DUAL II | 7.8 | 1.0 | LB A/A | | | | |
| | AFS-MTMS | | 0.5 | % V/V | | | | |
| 13 | Untreated | | | | | 0.0 | 0.0 | 0.0 |

TABLE 7-continued

| No. | Composition | Form Amt | Rate | Unit | Grow Stg | Weed Code: AMARE | AMBEL | ABUTH |
|---|---|---|---|---|---|---|---|---|
| | Treatment/Evaluation Interval | | | | | 30 DAP | 30 DAP | 30 DAP |
| | Date evaluated | | | | | Jun, 9, 1998 | Jun, 9, 1998 | Jun, 9, 1998 |
| | | | | | | Control Percent | | |
| LSD (P = 0.05) | | | | | | 4.16 | 2.16 | 2.89 |
| Standard Deviation | | | | | | 2.47 | 1.28 | 1.72 |
| CV | | | | | | 2.69 | 1.39 | 1.9 |

BALANCE - isoxaflutole;
DUAL II - metolachlor/benoxacor;
DAT—day after treatment;
DAP—day after planting;
AMARE redroot pigweed, *Amaranthus retroflexus* L;
AMBEL - common ragweed, *Ambrosia artemisiifolia* L.;
ABUTH - velvet-leaf, *Abutilon theophrasti* Medicus.

The results of Tables 6 and 7 are condensed in Table 8, which shows that the present invention prevented injury to corn caused by herbicide component of the composition without substantially affecting the ability of the herbicide component to control weed growth. Additional data was added to Table 8. The additional data shows that adding SMS or AFS-MTMS to the herbicide mixture prevented the herbicide component from affecting the growth of the corn. Also new in Table 8 is data showing that the herbicide mixture containing either SMS or AFS-MTMS did not substantially alter the herbicide component's ability to control the growth of giant foxtail (SETFA). Significantly, the grain yield of corn treated with the present invention was greater than the yields of corn treated with the herbicide mixture lacking either SMS or AFS-MTMS or the untreated controls.

Therefore, the results of the field trial show that the present invention renders the herbicides comprising the invention safe for use on corn while not reducing the ability of the herbicides comprising the present invention to control a wide variety of weeds.

TABLE 8

| Herbicide | Application Stage | Corn Injury[a] | Corn Height[b] | Weed Control[c] SETFA | CHEAL | AMARE | ABUTH | Grain Yield |
|---|---|---|---|---|---|---|---|---|
| | | -%- | -cm- | | | -%- | | kg/ha |
| Isoxaflutole[d] | 2-leaf | 0 | 61 | 73 | 95 | 98 | 99 | 10420 |
| Isoxaflutole + SMS[e] | 2-leaf | 0 | 61 | 72 | 96 | 98 | 100 | 10146 |
| Isoxaflutole + AFS-MTMS | 2-leaf | 0 | 61 | 56 | 85 | 92 | 100 | 10146 |
| Isoxaflutole + Metolachlor[fg] | 2-leaf | 50 | 41 | 95 | 100 | 100 | 100 | 9617 |
| Isoxaflutole + metolachlor + SMS | 2-leaf | 6 | 56 | 91 | 100 | 97 | 98 | 10277 |
| Isoxaflutole + metolachlor + AFS-MTMS | 2-leaf | 0 | 62 | 86 | 98 | 100 | 97 | 10527 |
| Isoxaflutole | 4-leaf | 10 | 61 | 70 | 96 | 100 | 100 | 9995 |
| Isoxaflutole + SMS | 4-leaf | 11 | 61 | 63 | 100 | 100 | 100 | 9881 |
| Isoxaflutole + AFS-MTMS | 4-leaf | 10 | 58 | 68 | 83 | 95 | 96 | 10728 |
| Isoxaflutole + Metolachlor[a] | 4-leaf | 83 | 32 | 95 | 100 | 100 | 98 | 9192 |
| Isoxaflutole + metolachlor + SMS | 4-leaf | 30 | 50 | 99 | 100 | 100 | 100 | 9508 |
| Isoxaflutole + metolachlor + AFS-MTMS | 4-leaf | 17 | 58 | 96 | 100 | 100 | 100 | 9993 |
| Untreated | | 0 | 64 | 0 | 0 | 0 | 0 | 8528 |
| $LSD_{50}$ | | 8 | 7 | 13 | 9 | 8 | 3 | 850 |

[a]Corn injury evaluated 30 DAP which was 21 days after 2-leaf application and 15 days after 4-leaf application.
[b]Corn height was measured 40 DAP.
[c]Weed control was evaluated 60 DAP.
[d]The rate of isoxaflutole was 105 g/ha.
[e]All adjuvants were applied at 0.5% v/v.
[f]The rate of metolachlor was 1121 g/ha.
[g]The formulation of metolachlor contained the herbicide safener benoxacor.

EXAMPLE 3

This example was performed as in Example 1, except that adjuvants SMS and AFS-MTMS were added to an isoxaflutole tank-mixture that contained an acetochlor herbicide and the safener MON-13900. As in Example 1, the herbicide applications were made to 2-leaf corn, and the herbicide treatments consisted of isoxaflutole at 105 g/ha and isoxaflutole tank-mixed with 1.8 kg/ha of acetochlor/MON-13900 applied either alone or in combination with either NIS at 0.25% (v/v), SMS at 0.5% (v/v), or AFS-MTMS at 0.5% (v/v).

The herbicide compositions were applied through an 8003 E flat fan nozzle delivering 234 L/ha at a pressure of 172 kPa. Corn tolerance was evaluated 8 DAT by visually evaluating the plants for bleaching and necrotic symptoms and also by measuring corn height (base of the plant to its crown). Visual corn injury ratings were based on a scale from 0 to 100, with 0 indicating no effect and 100 indicating plant death. Corn height was measured in cm and presented as a percent of the non-treated plants, with 0 indicating total reduction in plant height and 100 indicating height equal to the non-treated plants. All experiments were conducted twice as completely randomized designs with four replications. Data were subjected to analysis of variance and means separated using Fisher's Protected LSD test at a+0.05. Statistical analysis indicated no experimental run interactions, so the data were combined and reported as the means of two experiments. Non transformed means are presented since arcsine and square root transformations did not alter the interpretation of the data.

Table 9 shows the corn injury and height reductions as influenced by SMS or AFS-MTMS combined with isoxaflutole alone and in combination with acetochlor/MON-13900 when applied postemergence in the greenhouse. The table shows that the percent injury to corn treated with isoxaflutole in combination with acetochlor/MON-13900 was reduced to 20% when SMS was added to the combination. When AFS-MTMS was added to the combination of isoxaflutole and acetochlor/MON-13900 there was no visible injury to the corn. The table also shows that isoxaflutole in combination with acetochlor/MON-13900 reduced corn height by about 50% whereas adding either SMS or AFS-MTMS to the composition reduced the effect of the composition on corn height. In particular, in the presence of SMS, the height of the corn was reduced by only 20% and in the presence of AFS-MTMS, the height of the corn was virtually unaffected.

TABLE 9

| | | Injury[b] | | Height | |
|---|---|---|---|---|---|
| Treatment[a] | Rate | Isoxaflutole[c] | Isoxaflutole + acetochlor[d] | Isoxaflutole | Isoxaflutole + acetochlor[d] |
| | | -%- | | -% of control- | |
| Alone | | 0 | 64 | 99 | 47 |
| +NIS | 0.25% v/v | 13 | 68 | 88 | 45 |
| +SMS | 0.5% v/v | 0 | 20 | 100 | 79 |
| +AFS-MTMS | 0.5% v/v | 0 | 0 | 100 | 98 |
| $LSD_{0.05}$ | | -4- | | -8- | |

[a]Treatments were applied to 2-leaf (12) corn.
[b]Visual injury ratings and corn heights were evaluated 8 DAT.
[c]Isoxaflutole was applied at 105 g/ha.
[d]The formulation of acetolachlor contained the herbicide safener MON-13900 and was applied at 1.1 kg/ha.

EXAMPLE 4

This example was conducted to determine the effect of SMS and AFS-MTMS on foliar retention of isoxaflutole either alone or in combination with metolachlor/benoxacor. A version of the technique reported by Boldt and Putnam, Weed Science 28: 474–477 (1980) was used. Herbicide treatments examined were isoxaflutole applied alone at 105 g/ha and isoxaflutole tank-mixed with 1.1 kg/ha of metolachlor/benoxacor. Each of these herbicide treatments were applied alone or with either SMS or AFS-MTMS. The repellent adjuvants were each used at a rate of 0.5% v/v. The spray treatments, which included CHICAGO SKY BLUE (a product available from Sigma Chemical Co., St. Louis, Mo.) at 2.5 g/L, were applied to 2-leaf corn. Immediately after application, the whole plant was harvested and rinsed with distilled water containing the non-ionic surfactant X-77 (a product available from Valent U.S.A. Corp., Walnut Creek, Calif.) at 0.25% v/v. The absorbance of the rinsate was determine spectrophotometrically at 625 nm. Dye retention ($\mu$g/plant) was calculated from a standard curve.

Table 10 shows the spray retention of isoxaflutole as influenced by either SMS or AFS-MTMS, alone and in combination with metolachlor/benoxacor applied to 2-leaf corn in the greenhouse. The results show that neither SMS or AFS-MTMS increased the retention of isoxaflutole alone by the corn plant. The results further show that AFS-MTMS was particularly effective in reducing isoxaflutole retention when the composition further included metolachlor/benoxacor.

TABLE 10

| | | Spray retention | |
|---|---|---|---|
| Treatment | Rate | Isoxaflutole[a] | Isoxaflutole + metolachlor[b] |
| | | -$\mu$g of isoxaflutole/plant- | |
| Alone | | 4.4 | 15.1 |
| +SMS | 0.5% v/v | 5.8 | 17.3 |
| +AFS-MTMS | 0.5% v/v | 4.4 | 6.2 |
| $LSD_{0.05}$ | | -2.2- | |

[a]rates; isoxaflutole at 105 g/ha; metlachlor/benoxacor at 1.1 kg/ha.
[b]The formulation contained the herbicide safener benoxacor.

EXAMPLE 5

This example was to determine whether the adjuvants NIS, MTMS, SMS, AFS-MTMS, and PEAS affected weed control from early postemergence applications of isoxaflutole and isoxaflutole tank-mixed with metolachlor/benoxacor. Reduced rates of isoxaflutole (53 g/ha) and isoxaflutole tank-mixed with metolachlor/benoxacor (0.55 kg/ha) were applied alone and with either of NIS, MTMS, SMS, AFS-MTMS, or PEAS to 2-leaf velvetleaf (ABUTH) (3.5 to 5 cm) and 3-leaf barnyardgrass (5 to 10 cm). Velvetleaf and barnyardgrass controls were evaluated 21 DAT and shoots of both species were harvested to measure dry weight per pot. The results of this example are consistent with the weed control results presented in Tables 6, 7 and 8 of Example 2, which showed that the present invention was effective against weeds.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. A composition for application to cultivated plants to control weeds consisting essentially of:

(a) a herbicide which is injurious to the cultivated plants selected from the group consisting of acetanilides, acetamides, acetolactate synthase inhibitors, isoxazoles, diketonitriles, triketonitriles dinitroanilines, triazines, substituted ureas, ethofumerates, isoxafen, oxodiazon, dithiopyr;

(b) a safener which increases tolerance of the cultivated plants for the herbicide; and (c) repellent adjuvant which is a water soluable organic silain a water soluble organic silane for modifying surface properties of the composition so that retention of the composition on foliage of the cultivated plant is reduced, wherein the composition is applied in an aqueous solution as a spray and bounces off the plant into the soil and the composition to reduce herbicide injury to the cultivated plant by the herbicide and is effective from the soil around the plant to control the weeds.

2. The composition of claim 1 wherein the safener is selected from the group consisting of 4-(dichloroacetyl)-1-oxo-4-azaspiro-(4,5)-decane, 2,2-dichloro-N,N-di-2-propenylacetamide, 3-dichloroacetyl-5-(2-furanyl)-2,2-dimethyl-oxazolidine, 2,2,5-trimethyl-N-dichloroacetyloxazolidine, 2,2-dimethyl-5-phenyl-N-dichloroacetyl oxazolidine, N,N-diallyl-2,2-dichloroacetamide, 2,2-dimethyl-5(2-furanyl)-N-dichloroacetyl oxazolidine, 2,2-dimethyl-5 (2-thienyl)-N-dichloroacetyl oxazolidine, 2,2-spirocyclohexy-N-dichloroacetyl oxazolidine, 4-(dichloroacetyl)-3,4-dihydro-3-methyl-2H-1,4-benoxazine, 3-[3-(dichloroacetyl)-2,2-dimethyl-5-oxalidinyl]pyridine, 4-(dichloroacetyl)-1-oxa-4-azapiro-(4,5)-decane, 2,2-dichloro-1-(1,2,3,4-tetrahydro-1-methyl-2-isoquinolyl)ethanone, cis/trans-1,4-bis (dichloroacetyl)-2,5-dimethylpiperazine, N-(dichloroacetyl)-1,2,3,4-tetrahydroquinaldine, 1,5-bis(dichloroacetyl)-1,5-diazacyclonoonane and, 1-(dichloroacetyl)-1-azaspiro [4,4]nonane.

3. The composition of claim 1 wherein the herbicide is an isoxazole herbicide.

4. The composition of claim 3 wherein the herbicide is isoxaflutole.

5. The composition of claim 1 wherein the safener is selected from the group consisting of benoxacor, flurilizole, dichlormid and 4-(dichloroacetyl)-1-oxo-4-azaspiro-(4,5)-decane.

6. In a method for protecting crop plants including applying a herbicide formulation postemergence to the crop plant, the improvement comprising using as the herbicidal formulation a homogenous aqueous dispersion of the composition of claim 1.

7. In a method for protecting crop plants including applying a herbicide formulation that has herbicidal activity from soil, the improvement comprising using as the herbicidal formulation a homogenous aqueous dispersion of the composition of claim 3.

8. In a method for protecting crop plants includng applying a herbicide formulation postemergence to the crop plants, the improvement comprising using as the herbicidal formulation a homogenous aqueous dispersion of the composition of claim 2.

9. A method for controlling weeds around crop plants, the steps comprising:

(a) providing a herbicidal formulation consisting essentially of a herbicide which is injurious to the plants selected from the group consisting of acetanilides, acetamides, acetolactate synthase inhibitors, isoxazoles, diketonitriles, triketonitriles dinitroanilines, triazines, substituted ureas, ethofumerates, isoxafen, oxodiazon, dithiopyr cyclohexanidione, aryloxyphenoxy, imidazolinone, and sulfonylurea admixed with a safener which increases tolerance of the crop plants for the herbicide and a repellent adjuvant selected from the group consisting of silane, wherein the repellent adjuvant modifies surface properties of the formulation thereby reducing retention of the formulation on foliage of crop plants to reduce herbicide injury to the crop plant by the herbicide but which is effective from the soil;

(b) applying the formulation in an aqueous solution as a spray to the crop plants wherein the formulation bounces off the foliage onto the soil to control weeds around the plants without injuring the crop plants;

(c) optionally an oil-based adjuvant selected from the group consisting of a crop oil concentrate, a free fatty acid, an esterified and saponified oil and combinations thereof; and (d) optionally a monosaccharid to potentiate the effect of the herbicide in killing the weeds without decreasing tolerance of the crop plant to the herbicide.

10. The method of claim 9 wherein the safener is selected from the group consisting of 4-(dichloroacetyl)-1-oxo-4-azaspiro-(4,5)-decane, 2,2-dichloro-N,N-di-2-propenylacetamide, 3-dichloroacetyl-5-(2-furanyl)-2,2-dimethyl-oxazolidine, 2,2,5-trimethyl-N-dichloroacetyloxazolidine, 2,2-dimethyl-5-phenyl-N-dichloroacetyl oxazolidine, N,N-diallyl-2,2-dichloroacetamide, 2,2-dimethyl-5(2-furanyl)-N-dichloroacetyl oxazolidine, 2,2-dimethyl-5(2-thienyl)-N-dichloroacetyl oxazolidine, 2,2-spirocyclohexy-N-dichloroacetyl oxazolidine, 4-(dichloroacetyl)-3,4-dihydro-3-methyl-2H-1,4-benoxazine, 3-[3-(dichloroacetyl)-2,2-dimethyl-5-oxalidinyl]pyridine, 4-(dichloroacetyl)-1-oxa-4-azapiro-(4,5)decane, 2,2-dichloro-1-(1,2,3,4-tetrahydro-1-methyl-2-isoquinolyl)ethanone, cis/trans-1,4-bis (dichloroacetyl)-2,5-dimethylpiperazine, N-(dichloroacetyl)-1,2,3,4-tetrahydroquinaldine, 1,5-bis(dichloroacetyl)-1,5-diazacyclononane, 1-(dichloroacetyl)-1-azaspiro[4,4] nonane, and combinations thereof.

11. The method of claim 9 wherein the herbicide is an isoxazole herbicide.

12. The method of claim 11 wherein the herbicide is isoxaflutole.

13. The method of claim 9 wherein the oil-based adjuvant selected from the group consisting of a crop oil concentrate, a free fatty acid, an esterified and saponified oil and combinations thereof is present.

14. The method of claim 13 wherein the herbicide is selected from the group consisting of cyclohexanidione, aryloxyphenoxy, imidazolinone, and sulfonylurea herbicides.

15. The method of claim 9 wherein the composition further comprises a monosaccharide to potentiate the effect of the herbicide in killing the weed without decreasing tolerance of the crop plant to the herbicide.

16. A method for applying one or more postemergence herbicides for controlling weeds to a crop plant without injuring the crop plant, the steps comprising:

(a) providng a composition as a formulation consisting essentially of a herbicide which is injurious to the crop plant selected from the group consisting of acetanilides, acetamides, acetolactate synthase inhibitors, isoxazoles, diketonitriles, triketonitriles dinitroanilines, triazines, substituted ureas, ethofumerates, isoxafen, oxodiazon, and dithiopyr admixed with a repellent adjuvant which is a water soluble organic silane wherein the repellent adjuvant modifies surface properties of the formulation which is in an aqueous solution thereby reducing retention of the formulation on foliage of crop plants;

(b) a safener which increases tolerance of the crop plant for the herbicide; and (c) applying the formulation in the aqueous solution as a spray to the plants wherein the formulation bounces off the foliage onto the soil wherein the formlation controls the weeds without injuring the crop plant.

17. The method of claim 16 wherein the safener is selected from the group consisting of 4-(dichloroacetyl)-1-oxo-4-azaspiro-(4,5)-decane, 2,2-dichloro-N,N-di-2-propenylacetamide, 3-dichloroacetyl-5-(2-furanyl)-2,2-dimethyl-oxazolidine, 2,2,5-trimethyl-N-dichloroacetyloxazolidine, 2,2-dimethyl-5-phenyl-N-dichloroacetyl oxazolidine, N,N-diallyl-2,2-dichloroacetamide, 2,2-dimethyl-5(2-furanyl)-N-dichloroacetyl oxazolidine, 2,2-dimethyl-5(2-thienyl)-N-dichloroacetyl oxazolidine, 2,2-spirocyclohexy-N-dichloroacetyl oxazolidine, 4-(dichloroacetyl)-3,4-dihydro-3-methyl-2H-1,4-benoxazine, 3-[3-(dichloroacetyl)-2,2-dimethyl-5-oxalidinyl]pyridine, 4-(dichloroacetyl)-1-oxa-4-azapiro-(4,5)-decane, 2,2 -dichloro-1-(1,2,3,4-tetrahydro-1-methyl-2-isoquinolyl)ethanone, cis/trans-1,4-bis (dichloroacetyl)-2,5-dimethylpiperazine, N-(dichloroacetyl)-1,2,3,4-tetrahydroquinaldine, 1,5-bis(dichloroacetyl)-1,5-diazacyclononane and, 1-(dichloroacetyl)-1-azaspiro[4, 4]nonane, and combinations thereof.

* * * * *

UNITED STATES PATENT AND TRADEMARK OFFICE

CERTIFICATE OF CORRECTION

PATENT NO. : 6,936,569 B2
APPLICATION NO. : 09/9777320
DATED : August 30, 2005
INVENTOR(S) : Penner et al.

It is certified that error appears in the above-identified patent and that said Letters Patent is hereby corrected as shown below:

Cols 17 & 18
Table 6, in the headings, Columns 9, 10 & 11, "June 1, 1998" should be –June 9, 1998-.

Column 23, line 65, "acetolachlor" should be-acetochlor-.

Column 25, line 13, Claim 1, "silain a water soluble organic silane for modifying" should be –silane for modifying-.

Column 26, line 23, Claim 9, "monosaccharid" should be –monosaccharide-.

Column 28, line 14-15, Claim 17, after "[4,4] nonane." -,and combinations thereof– should be deleted.

Signed and Sealed this

Twenty-second Day of August, 2006

JON W. DUDAS
*Director of the United States Patent and Trademark Office*

UNITED STATES PATENT AND TRADEMARK OFFICE

CERTIFICATE OF CORRECTION

PATENT NO. : 6,936,569 B2
APPLICATION NO. : 09/777320
DATED : August 30, 2005
INVENTOR(S) : Penner et al.

It is certified that error appears in the above-identified patent and that said Letters Patent is hereby corrected as shown below:

Cols 17 & 18
Table 6, in the headings, Columns 9, 10 & 11, “June 1, 1998” should be –June 9, 1998-.

Column 23, line 65, “acetolachlor” should be-acetochlor-.

Column 25, line 13, Claim 1, “silain a water soluble organic silane for modifying” should be –silane for modifying-.

Column 26, line 23, Claim 9, “monosaccharid” should be –monosaccharide-.

Column 28, line 14-15, Claim 17, after “[4,4] nonane.” -,and combinations thereof– should be deleted.

This certificate supersedes Certificate of Correction issued August 22, 2006.

Signed and Sealed this

Tenth Day of October, 2006

JON W. DUDAS
*Director of the United States Patent and Trademark Office*